(12) United States Patent
Anquetil et al.

(10) Patent No.: US 11,701,468 B2
(45) Date of Patent: *Jul. 18, 2023

(54) METHOD AND DEVICE FOR DELIVERING SUBCUTANEOUS DOSE THROUGH MULTIPLE INJECTIONS

(71) Applicant: PORTAL INSTRUMENTS, INC., Cambridge, MA (US)

(72) Inventors: Patrick Armand Anquetil, Cambridge, MA (US); Ian Hunter, Lincoln, MA (US)

(73) Assignee: PORTAL INSTRUMENTS, INC., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,658

(22) Filed: Nov. 15, 2022

(65) Prior Publication Data

US 2023/0084655 A1    Mar. 16, 2023

Related U.S. Application Data

(63) Continuation of application No. 16/800,009, filed on Feb. 25, 2020, now Pat. No. 11,524,114, which is a
(Continued)

(51) Int. Cl.
*A61M 5/20* (2006.01)
*A61M 5/315* (2006.01)
(Continued)

(52) U.S. Cl.
CPC .............. *A61M 5/204* (2013.01); *A61M 5/24* (2013.01); *A61M 5/3134* (2013.01); *A61M 5/31535* (2013.01); *A61M 5/46* (2013.01);

*A61M 5/1409* (2013.01); *A61M 5/30* (2013.01); *A61M 5/3158* (2013.01); *A61M 5/31556* (2013.01);
(Continued)

(58) Field of Classification Search
CPC ...... A61M 5/204; A61M 5/24; A61M 5/3134; A61M 5/31535; A61M 5/1409; A61M 5/30; A61M 5/3007; A61M 5/3015; A61M 5/31556; A61M 5/31561; A61M 5/3158; A61M 2005/3022

See application file for complete search history.

(56) References Cited

U.S. PATENT DOCUMENTS

9,550,029 B2    1/2017 Boyden et al.
10,596,331 B2    3/2020 Kondo et al.
(Continued)

*Primary Examiner* — Dung T Ulsh
(74) *Attorney, Agent, or Firm* — Lando & Anastasi, LLP (57) ABSTRACT

A device for administering needle-free subcutaneous treatment to a patient comprises an actuator configured to deliver a plurality of volumes of a treatment at a plurality of locations on a body of the patient; at least one imaging device configured to detect a movement of the needle-free device from a first location on the body of the patient to a second location on the body of the patient; and a processor configured to determine the second location on the body of the device relative to the first location from the movement of the needle-free device relative to the first location on the body, the processor further configured to determine a volume of the plurality of volumes of the treatment to deliver to the body of the patient at the second location.

20 Claims, 6 Drawing Sheets

Related U.S. Application Data continuation of application No. 15/824,056, filed on Nov. 28, 2017, now Pat. No. 10,569,020.

(60) Provisional application No. 62/427,575, filed on Nov. 29, 2016.

(51) Int. Cl.
  *A61M 5/31* (2006.01)
  *A61M 5/24* (2006.01)
  *A61M 5/46* (2006.01)
  *A61M 5/14* (2006.01)
  *A61M 5/30* (2006.01)

(52) U.S. Cl.
  CPC .............. *A61M 5/31561* (2013.01); *A61M 2005/31588* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/6063* (2013.01)

(56) References Cited

U.S. PATENT DOCUMENTS

| | | | |
|---|---|---|---|
| 2008/0009788 A1* | 1/2008 | Hunter | A61M 5/3007 425/130 |
| 2011/0021905 A1* | 1/2011 | Patrick | A61M 5/16827 604/131 |
| 2012/0089114 A1* | 4/2012 | Hemond | A61M 5/46 604/500 |
| 2014/0322682 A1* | 10/2014 | Baym | G09B 5/02 340/5.6 |
| 2017/0080154 A1 | 3/2017 | Mudd et al. | |
| 2018/0056004 A1* | 3/2018 | Gamliel | A61M 5/46 |

* cited by examiner

METHOD AND DEVICE FOR DELIVERING SUBCUTANEOUS DOSE THROUGH MULTIPLE INJECTIONS

CROSS REFERENCE TO RELATED APPLICATIONS

This application claims the benefit under 35 U.S.C. § 120 as a continuation of U.S. application Ser. No. 16/800,009, filed Feb. 25, 2020, titled METHOD AND DEVICE FOR DELIVERING A SUBCUTANEOUS DOSE THROUGH MULTIPLE INJECTIONS and a continuation of U.S. application Ser. No. 15/824,056, filed Nov. 28, 2017, titled METHOD AND DEVICE FOR DELIVERING A SUBCUTANEOUS DOSE THROUGH MULTIPLE INJECTIONS, which claims priority under 35 U.S.C. § 119(e) to U.S. Provisional Application Ser. No. 62/427,575, titled "METHOD AND DEVICE FOR DELIVERING A SUBCUTANEOUS DOSE THROUGH MULTIPLE INJECTIONS," filed Nov. 29, 2016, which is incorporated herein by reference in its entirety.

BACKGROUND

Technical Field

The application relates generally to administering a dose of medicine via multiple injections, and more particularly, in one aspect, to systems and methods for tracking and controlling an amount of treatment injected by a needle-free injector at multiple sites on a patient.

SUMMARY

The methods and devices described herein overcome drawbacks of known approaches by controllably injecting a known volume of a treatment at multiple sites on the body to a controllable depth, including to intradermal, subdermal, or intramuscular treatment sites. In the embodiments described, a needle-free injector is used. As a user (e.g., a physician) moves the needle-free injector around a treatment site, the injector tracks its position and movement, for example, from the output of an accelerometer, gyroscope, and/or barometric sensor. This allows the injector to track the amount of treatment delivered at each location in a treatment "grid" or other treatment area. At each potential treatment location to which the injector is moved, the injector can determine an appropriate amount of treatment, if any, to be administered there based on prior injections of the current dose or earlier doses, the characteristics of the location, or other factors. The injector can then controllably deliver the treatment at the location or, alternately, restrain the actuator from delivering treatment at the location.

In some embodiments, an imaging sensor, such as a camera or sonogram device, may also be used to capture one or more images or sonograms of the treatment surface or potential treatment sites in the skin or the muscles beneath it. The images can then be processed to determine or verify the location of the injector. The images may also be used to identify intradermal, subdermal, or intramuscular treatment sites relevant to the treatment.

According to one aspect, a method of administering subcutaneous treatment to a patient is provided. The method includes delivering, by a needle-free injection device, a first volume of a treatment at a first location on a surface of a body of the patient; detecting a movement of the needle-free injection device relative to the first location; determining, from the movement of the needle-free injection device relative to the first location, a second location of the needle-free injection device relative to the first location; determining a second volume of the treatment to deliver at the surface of the body of the patient at the second location; and delivering, by the needle-free injection device, the second volume of the treatment at the second location on the surface of the body of the patient.

In one embodiment, the act of delivering, by the needle-free injection device, the first and second volumes of the treatment at the first and second locations on the surface of the body of the patient includes delivering the first and second volumes of the treatment to a first and second subcutaneous treatment site in the body of the patient. In a further embodiment, determining the second volume of the treatment is performed with reference to a previous treatment volume delivered to the second subcutaneous treatment site. In a further embodiment, each of the first subcutaneous treatment site and the second subcutaneous treatment site is one of an intradermal site, a subdermal site, and an intramuscular site.

In one embodiment, the method includes capturing, using a camera of the needle-free injection device, a first image of the surface of the body of the patient, wherein determining the second volume of the treatment is performed with reference to the first image of the surface of the body of the patient. In another embodiment, the method includes, responsive to determining that the previous treatment volume exceeds a predetermined value, determining that no treatment should be delivered to the second subcutaneous treatment site. In a further embodiment, the method includes disabling an actuator of the needle-free injection device from delivering the treatment to the second subcutaneous treatment site.

In another embodiment, the method includes capturing, using a camera of the needle-free injection device, a first image of the surface of the body of the patient, wherein determining the second location of the needle-free injection device relative to the first location is performed with reference to the first image of the surface of the body of the patient. In a further embodiment, the method includes identifying, in the first image of the surface of the body of the patient, the first location; capturing, using the camera of the needle-free injection device, a second image of the surface of the body of the patient; and identifying, in the second image of the surface of the body of the patient, the first location. In a still further embodiment, the method includes identifying, in the second image of the surface of the body of the patient, the second location. In a further embodiment, the second volume is determined with reference to a value determined from at least one of the first image and the second image.

In one embodiment, the act of detecting the movement of the needle-free injection device relative to the first location includes determining a displacement of the needle-free injection device with reference to an output of at least one of an accelerometer, a gyroscope, and a barometric sensor.

In another embodiment, the method includes storing, in a memory of the needle-free injection device, a first location value corresponding to the first location, and a second location value corresponding to the second location. In a further embodiment, the method includes storing, in the memory of the needle-free injection device, a plurality of values corresponding to a volume of treatment delivered at each of the first location and the second location. In a still further embodiment, the plurality of values is stored in a representation of an array.

In one embodiment, the method includes storing, in a memory of the needle-free injection device, a first location value corresponding to the first subcutaneous treatment site, and a second location value corresponding to the second subcutaneous treatment site.

In another embodiment, the method includes providing, via a user interface of the needle-free injection device, an indication that the needle-free injection device should be moved from one of the first location and the second location. In a further embodiment, the method includes providing, via a user interface of the needle-free injection device, an indication of a velocity at which the needle-free injection device should be moved from the first location to the second location.

In one embodiment, the method includes delivering at least one additional volume of the treatment at at least one additional location on the surface of the body of the patient, wherein the sum of the first volume, the second volume, and the at least one additional volume is substantially equal to a dose of the treatment.

In another embodiment, the method includes providing, by the needle-free injection device, an indication that needle-free injection device is at the second location. In a further embodiment, the indication is at least one of an audible indication, a visual indication, and a tactile indication.

In another embodiment, the method includes detecting that the needle-free injection device is substantially motionless at the second location. In yet another embodiment, the method includes providing, by the needle-free injection device, an indication that the needle-free injection device may be moved to a third location on the surface of the body of the patient. In still another embodiment, the method includes determining a distance between the first location and the second location, wherein determining the second volume of the treatment is performed with reference to the distance. In another embodiment, the treatment is a first treatment, and the method further includes delivering, by the needle-free injection device, a first and second volume of a second treatment at the respective first and second location on the surface of the body of the patient.

According to another aspect, a needle-free device for administering subcutaneous treatment to a patient is provided. The needle-free device includes an actuator configured to deliver a plurality of volumes of a treatment at a plurality of locations on a surface of a body of the patient; at least one sensor configured to detect a movement of the needle-free device from a first location on the surface of the body of the patient to a second location on the surface of the body of the patient; and a processor configured to determine, from the movement of the needle-free device relative to the first location, a second location of the device relative to the first location, and determine a volume of the treatment to deliver at the surface of the body of the patient at the second location.

According to one embodiment, the needle-free device includes a nozzle, wherein the actuator delivers the plurality of volumes of the treatments through the nozzle. According to a further embodiment, the actuator includes at least one of a Lorentz motor and an electromagnetic motor.

According to another embodiment, the processor is configured to determine the volume of the treatment to deliver at the surface of the body of the patient with reference to a previous treatment volume delivered at a subcutaneous treatment site adjacent the second location. According to a further embodiment, the processor is configured to determine, responsive to the previous treatment volume exceeding a predetermined value, that no treatment should be delivered to the subcutaneous treatment site. According to a still further embodiment, the processor is configured to prevent the actuator from delivering the treatment to the subcutaneous treatment site.

According to one embodiment, the needle-free device includes a camera configured to capture a plurality of images of the surface of the body of the patient. According to a further embodiment, the processor is configured to determine the second location of the needle-free device relative to the first location with reference to at least one of the plurality of images. According to a still further embodiment, the processor is configured to identify, in a first image of the plurality of images, the first location; and identify, in a second image of the plurality of images, the first location. In a further embodiment, the processor is configured to identify, in the second image of the plurality of images, the second location. In a still further embodiment, the volume is determined with reference to a value determined from at least one of the first image and the second image.

In one embodiment, the at least one sensor is at least one of an accelerometer, a gyroscope, and a barometric sensor. In another embodiment, the needle-free device includes a memory, wherein the processor is further configured to store in the memory a first location value corresponding to the first location and a second location value corresponding to the second location. In a still further embodiment, the processor is configured to store in the memory a plurality of values corresponding to a volume of treatment delivered at each of the first location and the second location. In yet a further embodiment, the processor is configured to store the plurality of values in a representation of an array.

In another embodiment, the needle-free device includes a plurality of nozzles, and the actuator delivers the plurality of volumes of the treatments through the plurality of nozzles.

In one embodiment, the needle-free device includes a user interface configured to provide an indication that the needle-free device should be moved from one of the first location and the second location. In a further embodiment, the user interface is configured to provide an indication of a velocity at which the needle-free device should be moved from the first location to the second location.

BRIEF DESCRIPTION OF DRAWINGS

Various aspects of at least one embodiment are discussed below with reference to the accompanying figures, which are not intended to be drawn to scale. The figures are included to provide an illustration and a further understanding of the various aspects and embodiments, and are incorporated in and constitute a part of this specification, but are not intended as a definition of the limits of any particular embodiment. The drawings, together with the remainder of the specification, serve to explain principles and operations of the described and claimed aspects and embodiments. In the figures, each identical or nearly identical component that is illustrated in various figures is represented by a like numeral. For purposes of clarity, not every component may be labeled in every figure. In the figures:

DESCRIPTION

Many treatment regimens call for the injection of large doses of a medicant or other treatment. For example, doses of botulinum toxin may be administered subcutaneously via hypodermic needle, auto-injector, or needle-free injector, either to treat muscle disorders or for cosmetic purposes. Such doses may be 2 to 3 mL, or larger. As another example, dental procedures may call for the administration of large doses of a numbing agent, such as procaine.

To increase their effectiveness and avoid pooling and other localized problems, large doses are often administered as a number of smaller injections. For example, injections may be administered at a number of locations corresponding to a grid array over a region of the patient's skin, or may be injected along one or more dimensions of a wrinkle or other feature that is being targeted.

The efficacy of manual injections of a treatment may be limited by a number of factors. For example, a physician manually actuating an injector of a hypodermic needle may have, at best, the dexterity to controllably administer an injection as small as 10 µL. Even where precise volumes of injections can be delivered, a physician administering a number of injections in a relatively small region is required to manually move the injector a small, precise distance to achieve an appropriate spacing for successive injections, to avoid administering multiple injections in the same location. The imprecision of this manual process again introduces accuracy and dexterity issues, and the possibility of inconsistent or suboptimal results.

According to one or more embodiments, methods and systems are provided for accurately delivering large doses via multiple injections from a needle-free injector. Such an injector may be used by a medical professional in a medical setting (e.g., a doctor's office) or by the patient (e.g., in the home). The injector is moved over a treatment region on the patient, such as the patient's forehead. A nozzle of the injector may inject the treatment at multiple locations in the treatment region.

The movement and orientation of the injector can be detected via sensors including an accelerometer, a gyroscope, a barometric sensor, or the like. The amount of movement can be used to determine a current position of the injector. The volume of treatment injected at each location can therefore be determined and stored. Because the depth of the injection is also controllable, it is possible to track the amount of treatment administered in three-dimensions. The injector can use this treatment location information to administer a large dose appropriately and precisely at a number of locations. For example, the total amount of the treatment previously delivered at a particular location may be used to determine how much additional treatment, if any, should be administered at that location. In some embodiments, a camera or sonogram device may be used to capture images of the treatment region, including the treatment surface (i.e., the skin through which the treatment will pass) and/or the treatment site (i.e., the subcutaneous location to where the treatment will be delivered). The images may be examined by the injector to determine its location in the treatment region, or to identify surface or subdermal regions for potential administration of treatment.

The injector includes an actuator, which may be a Lorentz-type or electromagnetic actuator. The actuator may be in communication with a cartridge, ampoule, or other receptacle for a treatment, which may be a liquid, a suspension, or a solid, such as a powder. By controlling a velocity and duration of the actuator's motion, the needle-free injector can deliver, repeatedly and with precision, an amount of the treatment to a subcutaneous treatment site in the patient.

The injector also includes at least one sensor, the output of which can be used to determine a location of the injector with respect to the treatment surface or treatment site. For example, an accelerometer may be included in the injector to detect when and how much the injector is accelerating. This information may be used to determine how far the injector has been moved, which can in turn be used to determine a current location of the injector. As another example, a gyroscope may be included in the injector to determine an orientation of the injector, which may be used to determine where the treatment is being delivered. As another example, a barometric sensor may be included in the injector to detect a current height (i.e., vertical position) of the injector. This information may be used to determine what part of the body (e.g., head as opposed to calves) will receive a current injection of the treatment.

In some embodiments, the injector may include an injector assembly that incorporates a nozzle through which the actuator delivers the treatment to the treatment site. The injector assembly may also incorporate the at least one sensor, so that the at least one sensor is near the treatment site when the treatment is about to be delivered.

A processor receives the output of the sensors, and uses it to determine the location of the device relative to a treatment region on the body of the patient. For example, the processor may be configured to determine the current location of the device relative to a first injection of the treatment, or other reference point. The processor uses this location information to track an amount of treatment delivered at a number of locations in the treatment site. This information may be used to determine how much treatment should be delivered at a current location of the device.

Consider an example where a large dose of 3 mL is administered as a number of smaller injections of 100 µL at each location in the treatment site. As the injector passes over each location in the treatment site, the processor may determine how much, if any, treatment to inject at that location. For example, on a first pass over a particular location, the processor may direct the actuator to inject 70 µL. On a second pass over the location, the processor may direct the actuator to inject only 30 µL to reach the total for the location of 100 µL. On a third pass over the location, the processor may prevent the actuator from injecting any further treatment at the location.

A user interface may also be provided to inform or direct a user of the injector. For example, the user interface may instruct the user (e.g., a doctor) to move the injector to a particular location in the treatment site, and/or to move the injector at a particular velocity, in a particular direction, etc. The user interface may also provide information to the user about a number of previous injections or suggested future injections. For example, a "heat map" may be displayed, with locations that have received the full amount of treatment in one color (e.g., red), and with locations that require further injections of treatment displayed in another color (e.g., green). In this way, the user interface can visually direct the user to move the injector to apply treatments to regions where it is necessary.

The injector may be provided as a device for use in a medical facility and having permanent reusable components and disposable components. For example, the actuator, user interface, and injector assembly may be part of a machine used in treatment/examination rooms by medical personnel. The machine may be configured to receive (e.g., in the injector assembly) a disposable single-dose assembly having a nozzle connected to an ampoule sized for a single dose of the treatment. The ampoule may be a fluid transport tube holding the treatment, connected at one end to the nozzle and configured to be removably connected at the other end to the actuator. In this way, single doses can be quickly and easily connected to the actuator to be delivered to a patient, with the single-dose assembly of the ampoule and nozzle being disposed of afterwards. A new single-dose assembly can be attached for use with the next patient, and so forth. In other embodiments, the injector may be provided as a handheld device suitable for use in outpatient care applications or other non-medical settings, such as the patient's home.

Figure 1:
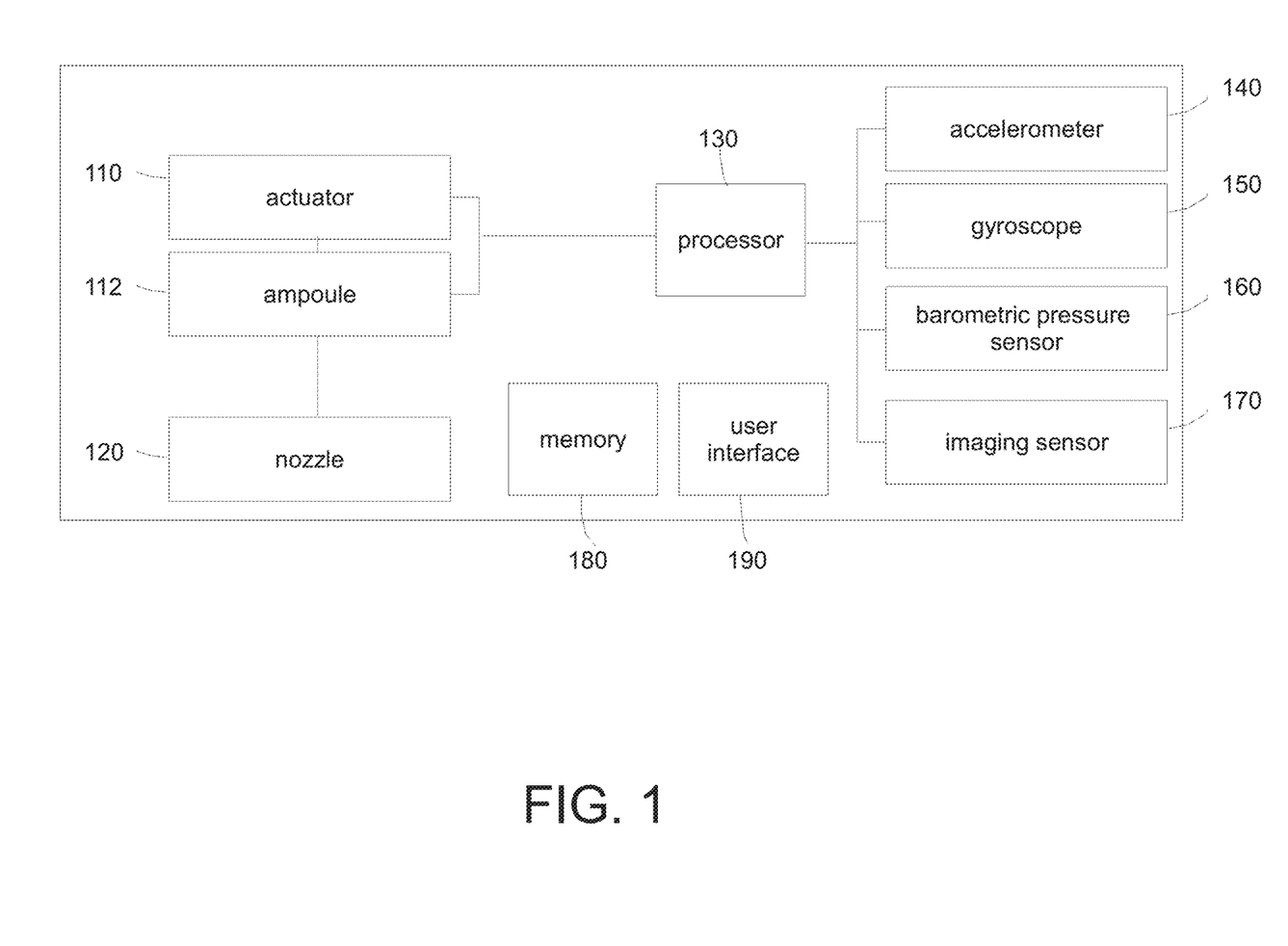
FIG. 1 is a block diagram of an injector for delivering a subcutaneous dose through multiple injections according to one or more embodiments.

FIG. 1 illustrates a block diagram of an injector 100 (e.g., a needle-free injector) according to one or more embodiments. In the embodiment shown in FIG. 1, the injector 100 includes an actuator 110 configured to deliver a treatment (e.g., a liquid or powder) from an ampoule 112 to a subcutaneous site of a patient via a nozzle 120. A processor 130 is configured to receive information from a number of sensors, including an accelerometer 140, a gyroscope 150, a barometric sensor 160, and an imaging sensor 170 (i.e., a camera), and to use that information to determine a current location of the nozzle 120 on a treatment surface (i.e., skin) of the patient. Using that location information, the processor 130 selectively controls the actuator 110 to deliver one or more volumes of the treatment to one or more treatment sites in the patient. A memory 180 is configured to store location information, as well as information about treatments administered at those locations.

A user interface 190 is configured to provide one or more indications regarding the location or desired movement of the injector 100. Such indications may be provided in an audible, visual, and/or tactile manner, and may indicate to the user of the injector that the nozzle 120 should be moved from a first location, that the nozzle 120 should be moved to a second location, that the nozzle 120 should be moved at a particular velocity, that the nozzle 120 should be held motionless at a location, or that the orientation of the nozzle 120 and/or the injector 100 should be changed.

Some or all of the components of the injector 100 may be disposed on or inside a housing (not shown). In some embodiments, the ampoule 112 and the nozzle 120 (or subcomponents thereof) may be a disposable assembly configured to be removably coupled to the actuator 110, allowing the injector 110 to be used for multiple patients.

The actuator 110 controllably generates an injection pressure to deliver a treatment through the skin to a subcutaneous treatment site of the patient. The actuator 110 may be configured to be operated manually (such as by a user pressing a button or trigger), and/or may operate automatically when the processor 130 determines that a treatment should be delivered. In some embodiments, the processor 130 may control the operation of the actuator 110 by allowing or disallowing an injection at a particular location or in a particular orientation. For example, the processor 130 may temporarily disable the actuator 110 when the nozzle 120 is positioned over a location at which a maximum amount of treatment has already been injected, or when the nozzle 120 is not engaged against the treatment surface. Once the nozzle 120 has been re-positioned at a suitable location, the processor 130 may re-enable the actuator 110.

The actuator 110 may be controlled by a servo-controller (not shown), which may be a motor that employs electromagnetic or Lorentz force. The actuator 110 may be of the type described in U.S. Pat. No. 8,740,838, titled "INJECTION METHODS USING A SERVO-CONTROLLED NEEDLE-FREE INJECTOR," issued on Jun. 3, 2014, the contents of which are hereby incorporated by reference in their entirety for all purposes. The processor 130 may obtain information from the actuator 110 during or after each injection event indicative of a volume of treatment delivered, one or more depths to which the treatment was delivered, and other information regarding the injection and/or the injection profile. The processor 130 may store that treatment information in the memory 180.

The ampoule 112 may taper at one end to form the nozzle 120, which is a hollow body having an inner diameter and a volume for effectively delivering the treatment to the subcutaneous site. Though the examples described herein use only one nozzle for ease of illustration, it will be appreciated that a plurality of nozzles may be employed. The nozzles may be disposed in a grid or array pattern, in a circular shape, in a line, or in other arrangement suitable for administering treatment.

The accelerometer 140 and/or the gyroscope 150, either alone or in combination, may provide to the processor 130 information regarding the orientation (e.g., tilt) and motion/acceleration of the phone. The information may relate to the instantaneous direction and magnitude of the orientation or motion. The accelerometer 140 and/or the gyroscope 150 may be provided as part of one or more microelectromechanical systems (MEMS) chips or components, and in a preferred embodiment may provide information on movement in three dimensions. Similarly, the barometric pressure sensor 160 may be used to measure atmospheric pressure in the ambient area around the injector 100. Information from the barometric pressure sensor 160 can be used to detect relative changes in the atmospheric pressure, which may indicate that the injector 100 has been moved vertically. This information, possibly in combination with the information from the accelerometer 140 and/or the gyroscope 150, can be used to detect and measure movement of the injector 100 in a vertical direction.

The imaging sensor 170 (i.e., camera) may be positioned near the nozzle 120 and configured and oriented to capture images of the treatment surface. The processor 130 may use the imaging sensor 170 to selectively capture images of the treatment surface periodically or upon detection of movement, or lack of movement, of the injector 100. The processor 130 may use the images to determine a current location of the nozzle 120 and/or the injector 100. For example, by detecting the relative movement of one or more features (e.g., moles) in subsequent images, the relative movement of the nozzle 120 can also be determined. In some embodiments, the features detected in the images may be grids, lines, or other features applied to the treatment surface to facilitate the use of the injector 100. The imagine sensor 170 may further comprise a sonogram sensor configured to capture one or more ultrasound images of the treatment surface or potential treatment sites in the skin or the muscles beneath it.

The processor 130 may correlate the injection information (e.g., volume of an injection event) received from the actuator 110 with the location information received from the accelerometer 140, the gyroscope 150, the barometric pressure sensor 160, and/or the imaging sensor 170 to determine how much treatment was delivered for a particular location on the treatment surface or a particular treatment site in the body. This information may be stored in the memory 180 to create a profile of some or all of the treatment region, with the profile storing the amount of treatment delivered at each location within the treatment region. For example, the memory 180 may store a two-dimensional array representing the treatment surface, with the amount of treatment delivered at each location on the treatment surface being stored at a corresponding position in the array. In another example, the memory 180 may store a three-dimensional array representing the treatment surface as well as the underlying potential treatment sites, with the amount of treatment delivered to each location being stored at a corresponding position in the array. In such embodiments, the x- and y-axes of the array may correspond to a latitude and longitude position on the treatment surface. The z-axis may correspond to a depth to which the treatment was injected.

Each position in the array may correspond to an area of a given dimension on the treatment surface. For example, each position in a two-dimensional array may correspond to an area of subcutaneous tissue of 1 mm$^2$. Similarly, each position in a three-dimensional array may correspond to a volume of subcutaneous tissue of 1 mm$^3$. It will be appreciated that these dimensions are given for illustrative purposes only, and that different dimensions may be used according to the treatment, condition being treated, or other factors.

For each location in the array, the memory 180 may store information including the amount of treatment delivered at the corresponding location; a remaining amount of treatment to be delivered at the corresponding location; a minimum or maximum amount of treatment to be delivered at the corresponding location; any information known about the location (e.g., the presence of any features such as moles, wrinkles, tumors, cysts, or the like); any information about previous injections or doses applied at the location; or other such information.

The user interface 190 may be used to guide, instruct, or otherwise provide information to the user (e.g., the patient or physician) regarding the use of the injector 100. Such information may be provided through audio, visual, and/or tactile elements of the user interface 190. For example, the user interface 190 may include a display screen configured to display text or other indications. The user interface 190 may also include a speaker configured to provide audible information to the user, such as tones or speech. The user interface may also include a tactile component configured to cause the injector 100 or components thereof to vibrate or buzz.

The user interface 190 may indicate that the user should move the nozzle 120 to or from a particular location. For example, a visual display may indicate that the user should move the nozzle 120 in a particular location on the treatment surface. The visual display may also indicate how fast the nozzle 120 should be moved, for example, by providing feedback on a current velocity of the nozzle 120. Where the nozzle 120 is being moved too quickly, for example, the user interface 190 may flash an indicator, buzz, or issue an audible alert for the user to move the nozzle 120 more slowly. In some embodiments, when the nozzle 120 has reached a location where treatment should be delivered, the user interface 190 may indicate that the user should stop moving the nozzle 120 and hold it motionless at a current location. The user interface 190 may indicate that the user should adjust an orientation of the nozzle 120 and/or the injector 100 by tilting or realigning the injector 100. The user interface 190 may also indicate that the user should activate the actuator 120, if necessary. After the treatment is delivered, the user interface 190 may indicate that the user may move the nozzle 120 again.

In some embodiments, the user interface 190 may be used to assist the injector 100 in re-locating a previous location. For example, in some embodiments a first treatment may be delivered at a first location and subsequent locations, and a second treatment may then be delivered at the first location and subsequent locations, making it necessary or desirable to re-locate the first location before administering the second treatment. In such examples, the user interface 190 may guide the user to move the nozzle 120 and/or the injector 100 generally through a series of motions, such as a spiral or series of concentric circles, to orient the device by re-locating the first location.

In operation, the injector 100 is moved around the treatment surface by the user. At each location, the injector 100 determines if an injection has already been delivered at that location, and if so, how much. Using this information, the injector 100 may determine an amount of treatment to currently deliver at that location, or may determine that no further treatment should be delivered at that location. If some amount of treatment is to be delivered, the processor 130 may cause or allow the actuator 110 to deliver the treatment, and may update the treatment information for that location accordingly.

Figure 2:
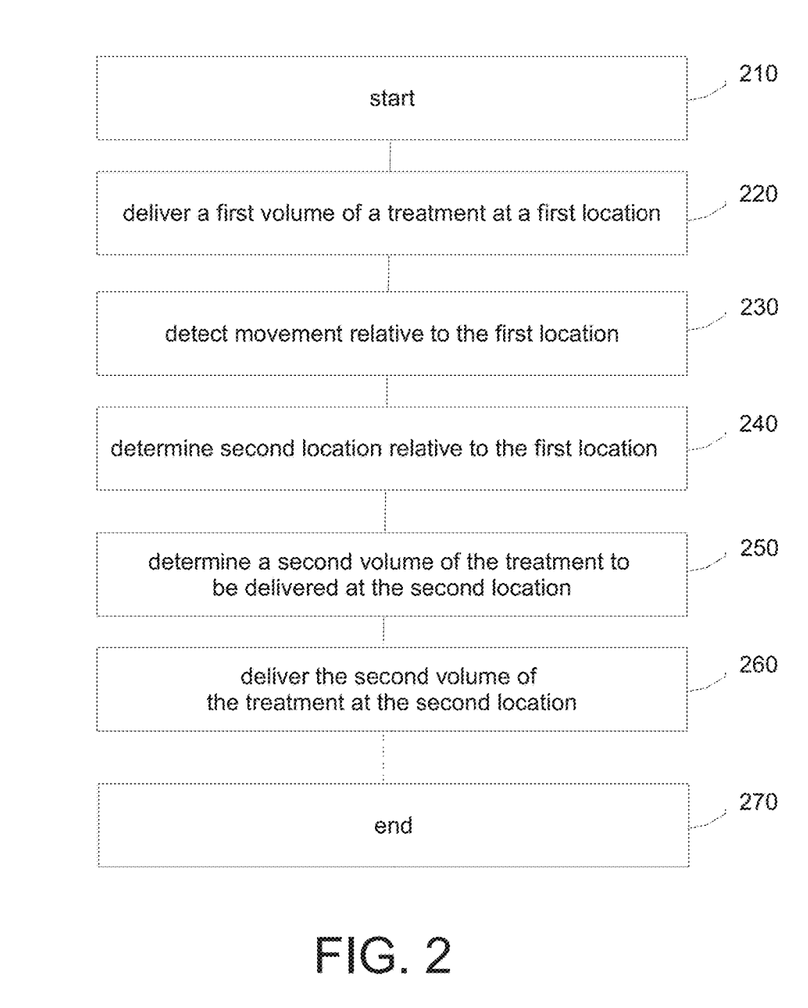
FIG. 2 is a flow chart of a method for using the injector according to one or more embodiments.

A method 200 of operating an injector (e.g., injector 100) according to some embodiments is described with reference to FIG. 2.

Method 200 begins at step 210.

At step 220, an injector delivers a first volume of a treatment at a first location on a surface of a body of the patient. As discussed above, an actuator delivers the treatment through the skin of the patient to a subcutaneous treatment site. The velocity and force of the injection may be controlled so that the subcutaneous site may be an intradermal site, a subdermal site, or an intramuscular site. The subcutaneous treatment site may be located directly underneath a corresponding location on the treatment surface and accessible most directly via an injection at that location and perpendicular to the treatment surface. It will be appreciated, however, that an injection may be delivered to the treatment site from another location at the treatment surface, with the injection delivered at an acute or obtuse angle to the treatment site.

At step 230, a movement of the needle-free injection device is detected relative to the first location. In some embodiments, the movement may be detected from information output by one or more sensors, including an accelerometer, gyroscope, barometric pressure sensor, camera, or otherwise. For example, an accelerometer may be included in the injector to detect when and how much the injector is accelerating. This information may be used to determine how far the injector has been moved. As another example, a gyroscope may be included in the injector to determine an orientation of the injector. For example, if the angle of a nozzle of the injector has changed due to the injector being tilted, a different subcutaneous treatment site may be aligned with the nozzle. As another example, a barometric sensor may be included in the injector to detect a current height (i.e., vertical position) of the injector. This information may be used to help determine what treatment site is aligned with the nozzle.

As will be discussed in more detail below, an imaging sensor may also be used to detect movement by capturing images of the treatment surface periodically or upon detection of movement, or lack of movement, of the injector. A relative movement of one or more treatment surface features in consecutive images may indicate movement.

At step 240, the movement of the injector detected in step 230 is used to determine a second location of the injector relative to the first location. For example, by examining the information from the accelerometer and gyroscope, it may be determined that the device moved at a known rate for a known amount of time in one or more known directions. This information can be used to determine the second location of the injector (after or during the movement) relative to the first location. The second location may be determined as an offset of the first location, and may be expressed and/or stored as a series of two- or three-dimensional coordinates representing the offset distance of the second location from the first location. In another example, the second location may be determined as an offset of the first location on a different coordinate scheme, such as on a polar coordinate system.

As will be discussed in more detail below, one or more images captured the output of the imaging sensor may be used to determine a current location of the injector. For example, by detecting the relative movement of one or more features (e.g., moles) in subsequent images, the relative movement of the nozzle can be determined.

At step 250, a second volume of the treatment to deliver at the surface of the body of the patient at the second location is determined. In one example, a memory having information about previous treatments at the second location may be accessed. For example, the memory may store a two-dimensional array or matrix representing the treatment surface, with the amount of treatment delivered at each location on the treatment surface being stored at a corresponding position in the array. In another example, the memory may store a three-dimensional array or matrix representing the treatment surface as well as the underlying potential treatment sites, with the amount of treatment delivered to each location being stored at a corresponding position in the array or matrix. In such embodiments, the x- and y-axes of the array or matrix may correspond to a latitude and longitude position on the treatment surface. The z-axis may correspond to a depth to which the treatment was injected.

In these examples, the location in the array or matrix corresponding to the second location may be accessed, and a current amount of treatment to be delivered at the second location or to a corresponding treatment site may be determined. For example, where no treatment has been delivered at the second location, it may be determined that a full location volume (i.e., the amount that would be injected at that location as part of a larger full dose) should be delivered. Where some amount of treatment less than the full location volume has already been delivered at the second location as part of a previous injection, it may be determined that a lesser amount should be delivered. Where the full location volume has already been delivered at the second location, it may be determined that no further treatment should be delivered at the second location.

The amount of treatment to be delivered at the second location may be made with reference to information about injections made as part of the current dose being administered, as well as information about doses that were administered in a previous time period, including the previous hour, day, week, month, year, etc. In one example, the amount of treatment to be delivered at the second location may be determined with reference to an amount of treatment delivered at the second location only as part of the current dose, which make take roughly 15 minutes to administer. In another example, the amount of treatment to be delivered at the second location may be determined with reference to an amount of treatment delivered at the second location within the previous month—that is, an injection may be withheld at the second location where it is determined that a full location volume was already injected there anytime within the previous 30 days. The amount of time, or the number of events, for which prior injection information is relevant may be configured by the user, or may be configured automatically according to the type of treatment and the dosing information.

It will be appreciated that because the injector may be configured to deliver treatment to different subcutaneous depths, the injector may track multiple volumes of treatment delivered at a single location to multiple treatment sites of varying depths. For example, the injector may be configured to deliver a certain volume to an intramuscular site underneath a treatment surface location on a first pass over the location, and on subsequent passes may deliver other volumes to subdermal and intradermal sites underneath the treatment surface location. In this manner, treatment can be vertically "stacked" within the subcutaneous layers.

Where it is determined that no treatment is to be delivered at the second location, the actuator may be temporarily disabled for a certain amount of time (e.g., enough time until the second location is able to receive further treatment), or until the injector has been moved to another location away from the second location.

At step 260, the injector delivers the second volume of the treatment at the second location on the surface of the body of the patient in much the same way as in step 220.

The exemplary method 200 describes injecting two volumes of treatment for ease of illustration, but it will be appreciated that the number of injections may typically be greater, such that the combined volume of all of the injections is substantially equal to the full dose amount. In some embodiments, therefore, some of the steps of method 200 may be repeated many (e.g., 50-100) times.

At step 270, method 200 ends.

As discussed above, an imaging sensor (i.e., a camera) may be used in some embodiments to capture one or more images of the treatment surface. The images may be used to determine or confirm a location of the injector relative to the treatment surface.

Figure 3:
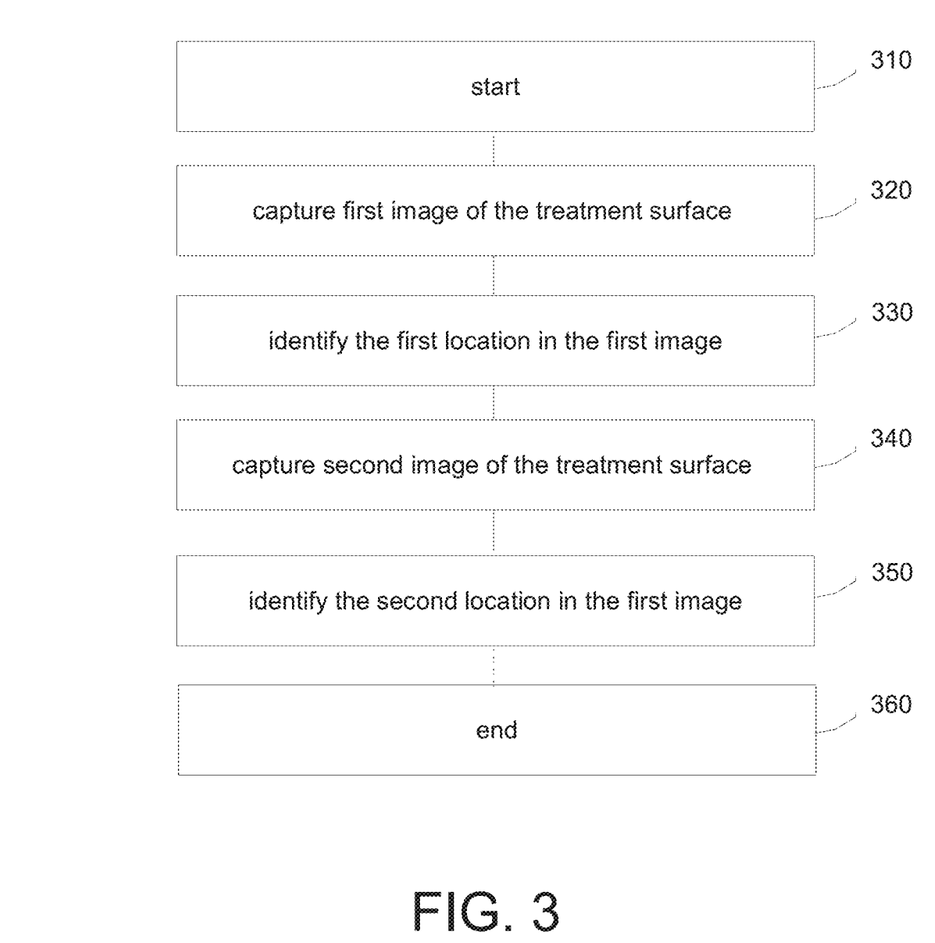
FIG. 3 is a flow chart of another method for using the injector according to one or more embodiments.

A method 300 of determining a location of the injector from one or more images according to some embodiments is described with reference to FIG. 3.

Method 300 begins at step 310.

At step 320, a first image of the surface of the body of the patient is captured, and at step 330, the first location is identified in the first image. In particular, the position of the first location in the image may be fixed and known, because the location of the nozzle relative to the camera may be fixed. In some embodiments, therefore, an appearance of the pixels corresponding to the first location may be determined, such as their color values and arrangement.

At step 340, a second image of the surface of the body of the patient is captured, and at step 350, the first location is identified in the second image. In particular, the second image may be examined for a collection of pixels having the appearance of the pixels corresponding to the first location in the first image. If those pixels are located in the second image, their location in the second image can be expected to correspond to the first location.

By determining the relative movement of the first location between the first image and the second image, a relative amount of movement of the injector can also be determined. This relative amount of movement can be used to determine or confirm the second location of the injector.

The exemplary method 300 describes capturing two images for ease of illustration, but it will be appreciated that the number of images may typically be greater as the injector is moved around the treatment surface.

Method 300 ends at step 360.

As discussed above, injectors in the present embodiments may incorporate user interfaces that instruct, guide, or otherwise provide the user with information regarding moving and positioning the injector on the treatment surface. A use case involving such user interfaces is discussed with reference to FIGS. 4A-4D.

Figure 4A:
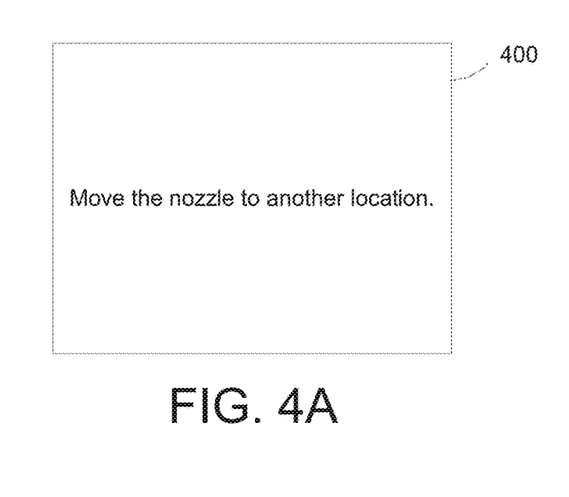
FIG. 4A is a representation of a user interface according to one or more embodiments.

In FIG. 4A, the injector is at a first location. The user interface 400 indicates that the user should begin moving the nozzle of the injector to another location. In some embodiments, the user interface 400 may display a directional indicator showing in which direction the nozzle should be moved. In other embodiments, a heatmap or other representation of the treatment surface or portions thereof may be displayed, with regions suitable for receiving injections as part of the current dose being shown in a corresponding color.

Figure 4B:
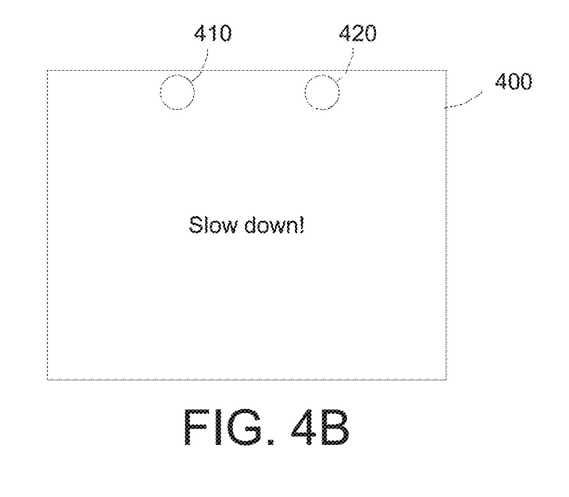
FIG. 4B is a representation of a user interface according to one or more embodiments.

In FIG. 4B, the user has begun moving the injector, but is moving it too quickly. The user interface 400 indicates that the user should move the injector more slowly. In some embodiments, visual indicators 410, 420 may flash or otherwise visually indicate that the injector is moving at an unsuitable speed. By contrast, where the injector is motionless, or is being moved at an appropriate speed, the visual indicators 410, 420 may flash in a different pattern, or may be solidly on or off.

Figure 4C:
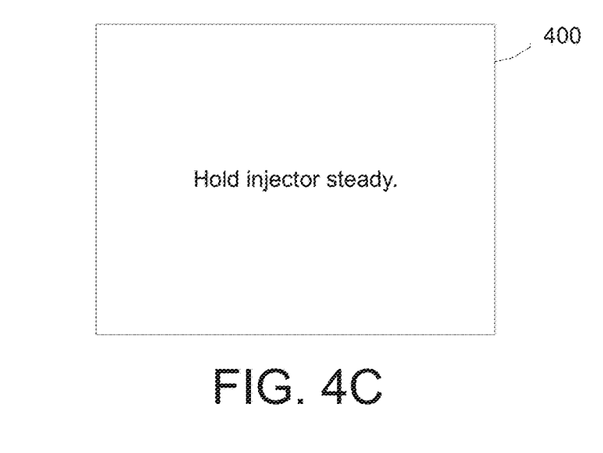
FIG. 4C is a representation of a user interface according to one or more embodiments.

In FIG. 4C, the injector has reached the second location, and the user interface 400 indicates that the user should hold the injector steady to prepare for an injection. As a safety measure, the injector may disallow injections while the injector is moving above a threshold amount.

Figure 4D:
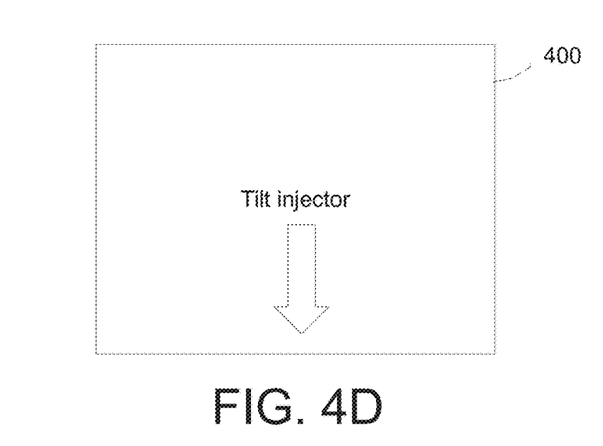
FIG. 4D is a representation of a user interface according to one or more embodiments.

In FIG. 4D, the injector has determined that the nozzle needs to be re-oriented to administer the injection, so the user interface 400 indicates that the user should tilt the injector. In some embodiment, a representation of a bubble level, or other indicator of angle, may be displayed to assist the user in achieving the proper angle. In some embodiments, a directional indicator may show in which direction the injector should be tilted, and by how much.

Once the injector is properly aligned, the user interface 400 may indicate that the user may administer the injection (e.g., by manipulating a trigger of the actuator), or the actuator may be configured to deliver the injection automatically when an appropriate location is reached and the appropriate orientation is achieved. After the injection is administered, the user interface 400 may return to the view in FIG. 4A, and indicate that the user may move the injector to another location.

In some embodiments, the injector may be an injector system for use in a medical setting, such as a physician's office. In such embodiments, the components of the injector system may be spread among a number of assemblies or housings. One or more components of the injector system (e.g., the ampoule and the nozzle) may be designed to be formed as a disposable single-dose assembly, allowing for re-use of the injector system with new, sanitized components for each patient.

Figure 5A:
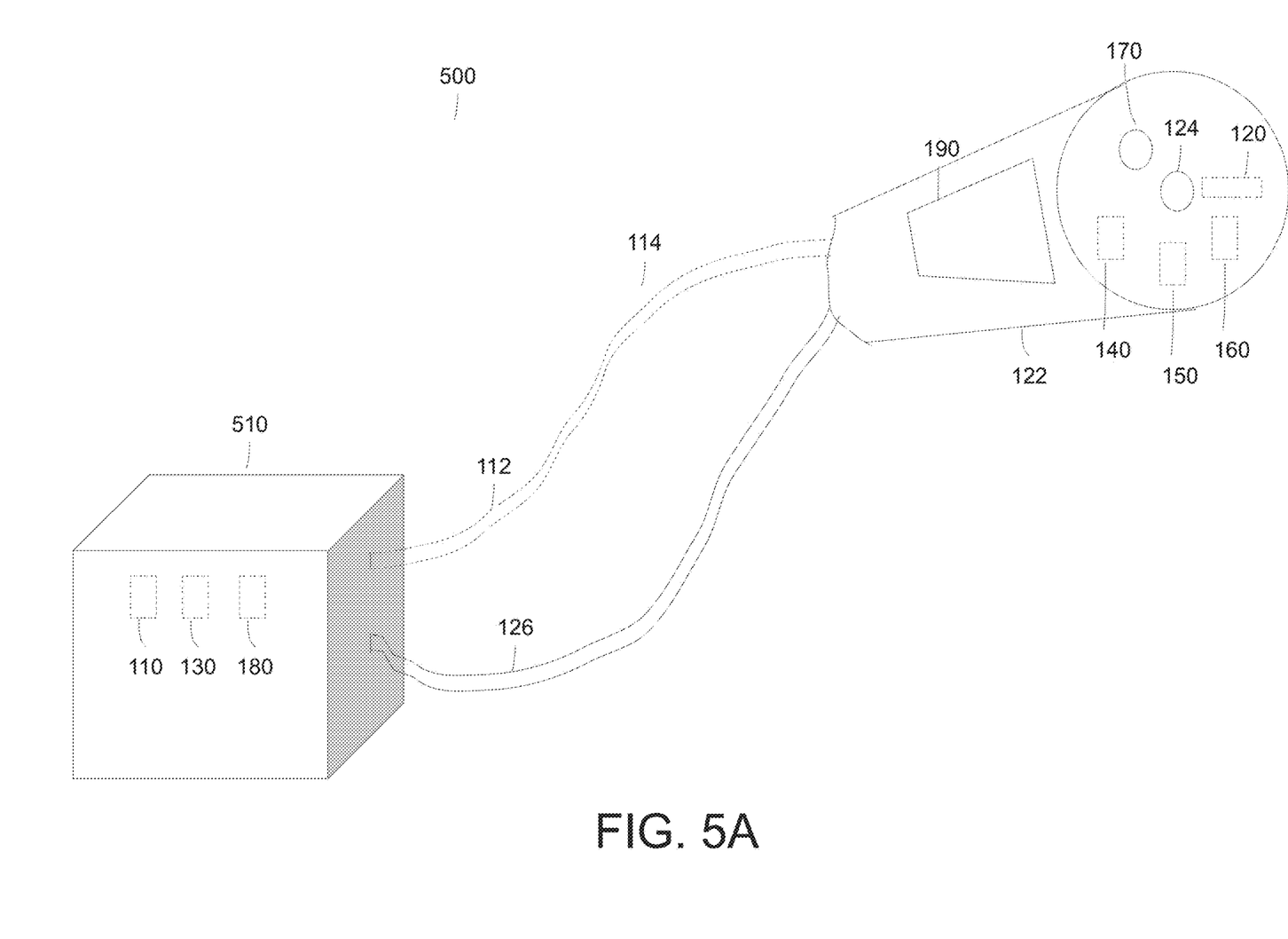
FIG. 5A is a representation of an injector according to one or more embodiments.
Figure 5B:
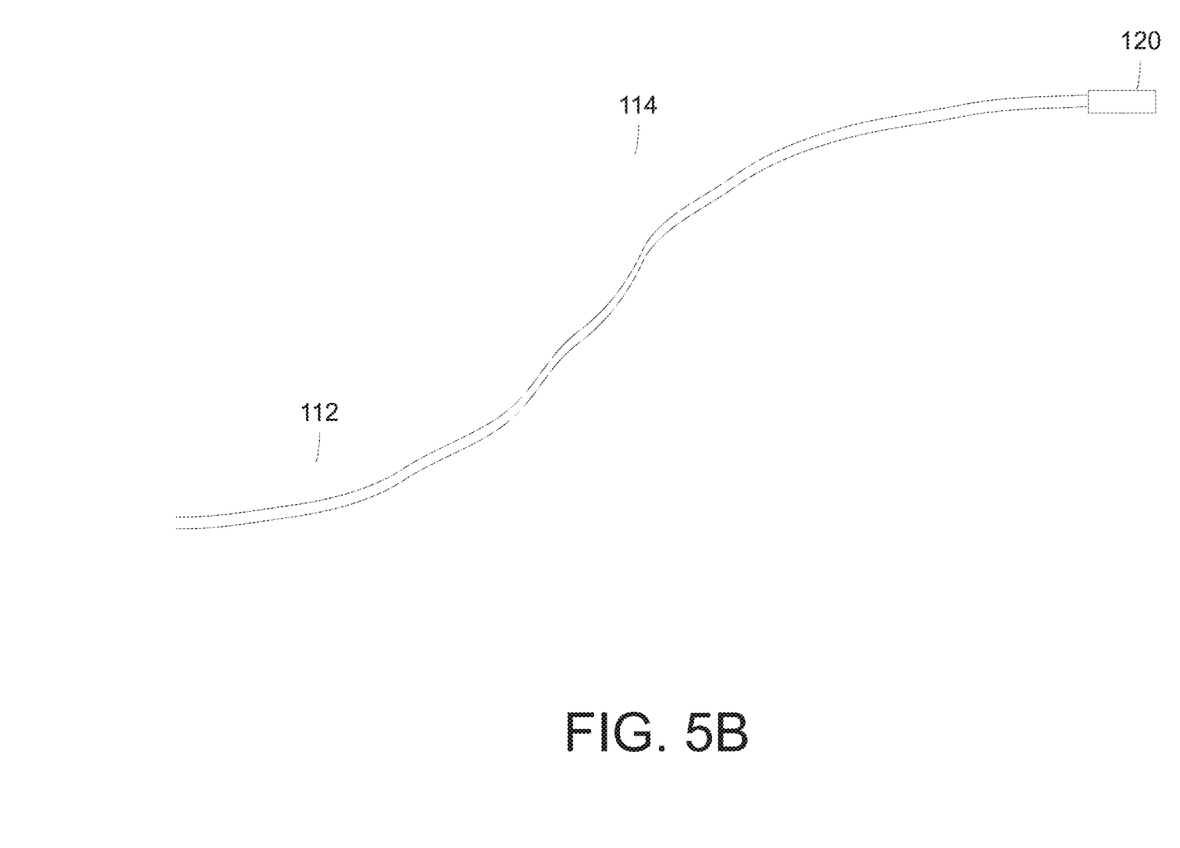
FIG. 5B is a representation of a single-dose assembly for use in an injector according to one or more embodiments.

An injector system 500 according to one or more embodiments is shown in FIGS. 5A and 5B. Except as described herein, the components described here function similarly to the counterpart components described above.

In the injector system 500, a number of components are included in an injector assembly 122, including an accelerometer 140, a gyroscope 150, a barometric sensor 160, an imaging sensor 170 (i.e., a camera), and a user interface 190. The injector assembly 122 is connected by means of one or more connectors 126 to other components in a housing 510, which may contain an actuator 110, a processor 130, and a memory 180. The one or more connectors 126 may be cables configured to allow the components in the injector assembly 122 to exchange information with the components in the housing 510.

In some embodiments, the injector assembly 122 is configured to receive a single-dose assembly 114 that includes a nozzle 120 connected to an ampoule 112 configured to connect to the actuator 130 in the housing 510. The injector assembly 122 may have a nozzle barrel 124 shaped to receive the nozzle 120 of the single-dose assembly 114 and hold the nozzle 120 in an orientation suitable for administering injections according to the embodiments described herein. Some or all of the ampoule 112 may contain one or more doses of a treatment to be administered through the nozzle 120 by the actuator 130. The nozzle 120 may be welded or otherwise sealed to the ampoule 112, making the single-dose assembly 114 a unitary disposable component suitable for sale separate from the injector system 500, as shown in FIG. 5B.

In other embodiments, the injector may be embodied in a handheld device. It will be appreciated that the embodiments described herein have a broad range of medical applications (including dental treatments) as well as cosmetic procedures.

As discussed above, aspects and functions disclosed herein may be implemented as hardware or software on one or more of these computer systems. There are many examples of computer systems that are currently in use. These examples include, among others, network appliances, personal computers, workstations, mainframes, networked clients, servers, media servers, application servers, database servers and web servers. Other examples of computer systems may include mobile computing devices, such as cellular phones and personal digital assistants, and network equipment, such as load balancers, routers and switches. Further, aspects may be located on a single computer system or may be distributed among a plurality of computer systems connected to one or more communications networks.

For example, various aspects and functions may be distributed among one or more computer systems configured to provide a service to one or more client computers. Additionally, aspects may be performed on a client-server or multi-tier system that includes components distributed among one or more server systems that perform various functions. Consequently, examples are not limited to executing on any particular system or group of systems. Further, aspects may be implemented in software, hardware or firmware, or any combination thereof. Thus, aspects may be implemented within methods, acts, systems, system elements and components using a variety of hardware and software configurations, and examples are not limited to any particular distributed architecture, network, or communication protocol.

The computer devices described herein are interconnected by, and may exchange data through, a communication network. The network may include any communication network through which computer systems may exchange data. To exchange data using the network, the computer systems and the network may use various methods, protocols and standards, including, among others, Fibre Channel, Token Ring, Ethernet, Wireless Ethernet, Bluetooth, Bluetooth Low Energy (BLE), IEEE 802.11, IP, IPV6, TCP/IP, UDP, DTN, HTTP, FTP, SNMP, SMS, MMS, SS7, JSON, SOAP, CORBA, REST and Web Services. To ensure data transfer is secure, the computer systems may transmit data via the network using a variety of security measures including, for example, TSL, SSL or VPN.

The computer systems include processors that may perform a series of instructions that result in manipulated data. The processor may be a commercially available processor such as an Intel Xeon, Itanium, Core, Celeron, Pentium, AMD Opteron, Sun UltraSPARC, IBM Power5+, or IBM mainframe chip, but may be any type of processor, multi-processor or controller.

A memory may be used for storing programs and data during operation of the device. Thus, the memory may be a relatively high performance, volatile, random access memory such as a dynamic random access memory (DRAM) or static memory (SRAM). However, the memory may include any device for storing data, such as a disk drive or other non-volatile storage device. Various examples may organize the memory into particularized and, in some cases, unique structures to perform the functions disclosed herein.

The devices may also include one or more interface devices such as input devices and output devices. Interface devices may receive input or provide output. More particularly, output devices may render information for external presentation. Input devices may accept information from external sources. Examples of interface devices include keyboards, mouse devices, trackballs, microphones, touch screens, printing devices, display screens, speakers, network interface cards, etc. Interface devices allow the computer system to exchange information and communicate with external entities, such as users and other systems.

Data storage may include a computer readable and writeable nonvolatile (non-transitory) data storage medium in which instructions are stored that define a program that may be executed by the processor. The data storage also may include information that is recorded, on or in, the medium, and this information may be processed by the processor during execution of the program. More specifically, the information may be stored in one or more data structures specifically configured to conserve storage space or increase data exchange performance. The instructions may be persistently stored as encoded signals, and the instructions may cause the processor to perform any of the functions described herein. The medium may, for example, be optical disk, magnetic disk or flash memory, among others. In operation, the processor or some other controller may cause data to be read from the nonvolatile recording medium into another memory, such as the memory, that allows for faster access to the information by the processor than does the storage medium included in the data storage. The memory may be located in the data storage or in the memory, however, the processor may manipulate the data within the memory, and then copy the data to the storage medium associated with the data storage after processing is completed. A variety of components may manage data movement between the storage medium and other memory elements and examples are not limited to particular data management components. Further, examples are not limited to a particular memory system or data storage system.

Various aspects and functions may be practiced on one or more computers having a different architectures or components than that shown in the Figures. For instance, one or more components may include specially programmed, special-purpose hardware, such as for example, an application-specific integrated circuit (ASIC) tailored to perform a particular operation disclosed herein. While another example may perform the same function using a grid of several general-purpose computing devices running MAC OS System X with Motorola PowerPC processors and several specialized computing devices running proprietary hardware and operating systems.

One or more components may include an operating system that manages at least a portion of the hardware elements described herein. A processor or controller may execute an operating system which may be, for example, a Windows-based operating system, such as, Windows NT, Windows 2000 (Windows ME), Windows XP, Windows Vista or Windows 7 operating systems, available from the Microsoft Corporation, a MAC OS System X operating system available from Apple Computer, an Android operating system available from Google, one of many Linux-based operating system distributions, for example, the Enterprise Linux operating system available from Red Hat Inc., a Solaris operating system available from Oracle Corporation, or a UNIX operating systems available from various sources. Many other operating systems may be used, and examples are not limited to any particular implementation.

The processor and operating system together define a computer platform for which application programs in high-level programming languages may be written. These component applications may be executable, intermediate, byte-code or interpreted code which communicates over a communication network, for example, the Internet, using a communication protocol, for example, TCP/IP. Similarly, aspects may be implemented using an object-oriented programming language, such as .Net, SmallTalk, Java, C++, Ada, or C# (C-Sharp). Other object-oriented programming languages may also be used. Alternatively, functional, scripting, or logical programming languages may be used.

Additionally, various aspects and functions may be implemented in a non-programmed environment, for example, documents created in HTML, XML or other format that, when viewed in a window of a browser program, render aspects of a graphical-user interface or perform other functions. Further, various examples may be implemented as programmed or non-programmed elements, or any combination thereof. For example, a web page may be implemented using HTML while a data object called from within the web page may be written in C++. Thus, the examples are not limited to a specific programming language and any suitable programming language could be used. Thus, functional components disclosed herein may include a wide variety of elements, e.g. executable code, data structures or objects, configured to perform described functions.

What is claimed is:
1. A device for administering needle-free subcutaneous treatment to a patient comprising:
an actuator configured to deliver a plurality of volumes of a treatment at a plurality of locations on a body of the patient;

at least one imaging device configured to detect a movement of the needle-free device from a first location on the body of the patient to a second location on the body of the patient; and a processor configured to determine the second location on the body of the device relative to the first location from the movement of the needle-free device relative to the first location on the body, the processor further configured to determine a volume of the plurality of volumes of the treatment to deliver to the body of the patient at the second location.

2. The device of claim 1, wherein the imaging device includes a camera configured and oriented to capture images of a treatment surface of the patient.

3. The device of claim 1, wherein the imaging device includes a sonogram device.

4. The device of claim 1, wherein the imaging device includes an imaging sensor.

5. The device of claim 1, wherein the imaging device includes an ultrasound imaging device.

6. The device of claim 1, wherein the imaging device includes one or more sensors configured to capture images of a potential treatment site beneath a surface of the body.

7. The device of claim 1, further comprising a nozzle for needle-free delivery of the treatment, wherein the actuator delivers the plurality of volumes of the treatment through the nozzle.

8. The device of claim 1, further comprising a camera configured to capture a plurality of images of a surface of the body of the patient.

9. The device of claim 8, wherein the processor is further configured to: identify the first location in a first image of the plurality of images and a second image of the plurality of images.

10. The device of claim 9, wherein the processor is further configured to identify, in the second image of the plurality of images, the second location.

11. The device of claim 1, wherein the actuator includes at least one of a Lorentz motor and an electromagnetic motor.

12. The device of claim 1, wherein the processor is further configured to determine the volume of the treatment for delivery to the body of the patient at the second location with reference to a previous treatment volume delivered at a subcutaneous treatment site adjacent to the second location.

13. The device of claim 1, further comprising at least one other sensor for detecting the movement, the at least one other sensor including one or more of an accelerometer and a gyroscope.

14. The device of claim 1, further comprising a memory, wherein the processor is further configured to store in the memory a first location value corresponding to the first location and a second location value corresponding to the second location, and to store in the memory a plurality of values corresponding to a volume of treatment delivered at each of the first location and the second location.

15. The device of claim 1, further comprising a plurality of nozzles, wherein the actuator delivers the plurality of volumes of the treatment through the plurality of nozzles.

16. The device of claim 1, further comprising a user interface configured to provide an indication that the needle-free device should be moved from one of the first location and the second location.

17. The device of claim 16, wherein the user interface is further configured to provide a second indication of a velocity at which the needle-free device should be moved from the first location to the second location.

18. An injector for administering subcutaneous treatment to a patient, the injector comprising:

a nozzle;

a reservoir configured to contain a treatment;

an actuator configured for needle-free delivery of a plurality of volumes of the treatment through the nozzle at a plurality of locations on a body of the patient;

at least one imaging device configured to capture a first image and a second image during a motion of the injector; and a processor configured by computer executable code to perform the steps of:

detecting, based on the first image and the second image, a movement of the injector from a first location on the body of the patient to a second location on the body of the patient, determining a volume of the plurality of volumes of the treatment to deliver to the second location, and causing the actuator to deliver the volume to the second location on the body.

19. The device of claim 18, wherein the at least one imaging device is configured to capture images of a treatment surface of the patient.

20. The device of claim 18, wherein the at least one imaging device is configured to capture images of a potential treatment site beneath a surface of the body.

* * * * *